US010395178B2

(12) United States Patent
Chen

(10) Patent No.: US 10,395,178 B2
(45) Date of Patent: Aug. 27, 2019

(54) RISK ASSESSMENT SYSTEM AND DATA PROCESSING METHOD

(71) Applicant: Wistron Corporation, New Taipei (TW)

(72) Inventor: Chih-Ming Chen, New Taipei (TW)

(73) Assignee: Wistron Corporation, New Taipei (TW)

(*) Notice: Subject to any disclaimer, the term of this patent is extended or adjusted under 35 U.S.C. 154(b) by 739 days.

(21) Appl. No.: 14/936,683

(22) Filed: Nov. 10, 2015

(65) Prior Publication Data

US 2017/0039479 A1 Feb. 9, 2017

(30) Foreign Application Priority Data

Aug. 7, 2015 (TW) .............................. 104125825 A

(51) Int. Cl.
*G06N 7/00* (2006.01)
*G16H 50/30* (2018.01)
*G16H 50/20* (2018.01)

(52) U.S. Cl.
CPC ............. *G06N 7/005* (2013.01); *G16H 50/20* (2018.01); *G16H 50/30* (2018.01)

(58) Field of Classification Search
USPC ........................................................ 706/12
See application file for complete search history.

(56) References Cited

U.S. PATENT DOCUMENTS

| 8,200,506 B2 | 6/2012 | Kil |
| 8,694,300 B2 | 4/2014 | Morris et al. |
| 9,203,804 B2* | 12/2015 | Chen ................. H04L 63/0227 |
| 9,305,317 B2* | 4/2016 | Grokop ................. B60W 40/09 |
| 9,477,429 B2* | 10/2016 | Chen ..................... G06F 3/0619 |
| 9,479,485 B2* | 10/2016 | Chen ................... H04L 63/0428 |
| 9,736,187 B2* | 8/2017 | Chen ........................ H04L 63/20 |
| 9,811,278 B2* | 11/2017 | Chen ..................... G06F 3/0622 |
| 9,813,438 B2* | 11/2017 | Chen ................... H04L 63/1425 |

(Continued)

OTHER PUBLICATIONS

IEEE Supporting Software Release Planning Decisions for Evolving Systems O. Saliu; G. Ruhe Published in: 29th Annual IEEE/NASA Software Engineering Workshop Date of Conference: Apr. 6-7, 2005 IEEE.*

(Continued)

*Primary Examiner* — Michael B Holmes
(74) *Attorney, Agent, or Firm* — JCIPRNET

(57) ABSTRACT

A risk assessment system and a data processing method are provided. The risk assessment system includes an analyze device and an electronic device. The analyze device generates at least one decision table according to a plurality of data and context features of the plurality of data. Each of the decision table has a plurality of entries, and each of the entries includes at least one of determining condition and probability information corresponding to a specific result. The electronic device communicates with the analyze device. The electronic device receives the decision table and compares the determining conditions of each entries with current conditions of an assessee. When the current conditions are the same to the determining conditions of a specific entry, the electronic device displays the determining conditions and the probability information corresponding to the specific entry.

25 Claims, 2 Drawing Sheets

(56) References Cited

U.S. PATENT DOCUMENTS

| | | | | |
|---|---|---|---|---|
| 9,973,471 | B2* | 5/2018 | Chen | H04L 63/02 |
| 9,979,778 | B2* | 5/2018 | Lee | H04L 67/10 |
| 9,996,376 | B2* | 6/2018 | Chen | G06F 9/45558 |
| 10,075,477 | B2* | 9/2018 | Chen | H04L 63/205 |
| 10,079,840 | B2* | 9/2018 | Chen | H04L 63/1416 |
| 10,147,048 | B2* | 12/2018 | Chen | G06F 11/00 |
| 10,175,051 | B2* | 1/2019 | Chen | H04W 4/33 |
| 2005/0160324 | A1 | 7/2005 | Przytula et al. | |
| 2006/0129427 | A1 | 6/2006 | Wennberg | |
| 2015/0120336 | A1* | 4/2015 | Grokop | B60W 40/09 |
| | | | | 705/4 |

OTHER PUBLICATIONS

ScienceDirect Elsevier Expert Systems with Applications vol. 36, Issue 6, Aug. 2009, pp. 9879-9890 Assessing new product development project risk by Bayesian network with a systematic probability generation methodology Kwai-Sang Chin, Da-Wei Tang, Jian-Bo Yang, Shui Yee Wong, Hongwei Wang.*

ScienceDirect Elsevier European Journal of Operational Research vol. 196, Issue 2, Jul. 16, 2009, pp. 401-412 Facility location and supply chain management—A review M.T. Melo, S. Nickel, F. Saldanha-da-Gama.*

"Office Action of Taiwan Counterpart Application" with English translation thereof, dated Nov. 10, 2016, p. 1-p. 12, in which the listed references was cited.

Lucas et al. "Bayesian analysis, pattern analysis, and data mining in health care." Current Opinion in Critical Care, Oct. 2004, 399-403.

Letham et al., "Interpretable classifiers using rules and Bayesian analysis: Building a better stroke prediction model," University of Washington, Department of Statistics, Technical Report No. 609, Aug. 2013, pp. 1-22.

* cited by examiner

RISK ASSESSMENT SYSTEM AND DATA PROCESSING METHOD

CROSS-REFERENCE TO RELATED APPLICATION

This application claims the priority benefit of Taiwan application serial no. 104125825, filed on Aug. 7, 2015. The entirety of the above-mentioned patent application is hereby incorporated by reference herein and made a part of this specification.

BACKGROUND OF THE INVENTION

Field of the Invention

The invention relates to a technique of performing data statistics and risk assessment on assessee information, and particularly relates to a risk assessment system and a data processing method.

Description of Related Art

To use historic data to study and determine whether specific human behaviors may influence human body or psychological status to cause probabilistic pathological changes or criminal acts is a goal to be achieved since ancient times. By achieving the above goal, data of a group of people may be collected to decrease a risk of illness or prevent crimes occurred in the group of people. On a medical point of view, if it determined that a specific disease is very possible to be directly related to specific conditions according to medical record data of a group of people, a doctor may provide suggestions or provide corresponding medicines for life behaviors of different patients or certain diseases, such that by ameliorating life behaviors or taking specific medicines, a chance that the patient falls ill is decreased or the pain brought by the disease is relieved.

The conventional risk assessment techniques all adopt a score measuring system provided by experts in collaboration with medical records of an assessee (for example, a patient) or questionnaires to describe pathology probability of the assessee for the specific disease or risk assessment of crime probability in model formulas. However, the aforementioned model formulas only adopt opinions or views of the experts, and are hard to describe why the specific disease is induced or a crime risk is increased through conditions therein. For example, a doctor may only explain the probability or a risk level of the specific disease vaguely to the patient based on the score measuring system, but cannot clearly explain the specific conditions that increases the possibility of the disease. On the other hand, the current risk assessment technique generally adopts a complicated and inaccurate algorithm (for example, a greedy construction method, a classification and regression trees algorithm, a decision tree learning algorithm, etc.) to acquire a calculation result. However, in an actual application, the greedy construction method is very possible to only obtain a local optimization result due to inadequate data types, and cannot achieve global optimization.

SUMMARY OF THE INVENTION

The invention is directed to a risk assessment system and a data processing method, by which a risk assessing effect is achieved based on context features of data and a model algorithm with low complexity, so as to improve usage efficiency.

The invention provides a risk assessment system including an analysis device and an electronic device. The analysis device generates at least one decision table according to a plurality of data and context features of the plurality of data. Each of the decision tables has a plurality of entries, and each of the entries includes at least one determining condition and probability information corresponding to a specific result. The electronic device communicates with the analysis device. The electronic device receives the decision table and compares the determining conditions of each of the entries in the decision tables with at least one current condition of an assessee. Moreover, when the current conditions are the same with the determining conditions of a specific entry, the electronic device displays the determining conditions and the probability information corresponding to the specific entry.

The invention provides a data processing method, which includes following steps. At least one decision table is generated according to a plurality of data and context features of the plurality of data. Each of the decision tables has a plurality of entries, and each of the entries includes at least one determining condition and probability information corresponding to a specific result. The determining conditions of each of the entries in the decision table are compared with at least one current condition of an assessee. Moreover, when the current conditions are the same with the determining conditions of a specific entry, the determining conditions and the probability information corresponding to the specific entry are displayed.

According to the above description, in the risk assessment system and the data processing method of the invention, a risk assessing effect is achieved based on context features of data and a model algorithm with low complexity, so as to improve usage efficiency. On the other hand, a professional in the field such as a doctor may explain a risk assessment reason and a prevention method of a specific event to the assessee or patient through the determining conditions, such that the risk assessment system is easy to use.

In order to make the aforementioned and other features and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

In an embodiment of the invention, a decision alignment method is used to estimate risks of specific situations (for example, a specific disease or reoccurrence probability of a specific crime) for an assessee in a specific domain (for example, a medical field or crime prevention field). In the embodiment of the invention, a medical care field is taken as an example for description. It is hoped to build a risk assessment platform, a system and a data processing method, such that a doctor may easily sort occurrence probabilities of certain disease of a patient in a priority order from a high risk to a low risk based on a small number of determining conditions, so as to provide corresponding suggestions or provide corresponding medicines or medical treatment to each of the patients according to their own conditions. Moreover, the risk assessment platform may also be applied to other technical fields hoping to perform statistics and risk assessment on people's behaviors or situations, for example, the crime prevention field. In other words, the risk assessment platform and the system thereof hope to decrease constructing cost in medical use or crime prevention use, so as to decrease dependence on hardware computation by decreasing a computation difficulty of the model algorithm, and accordingly increase a usage efficiency of the risk assessment platform used by the professionals in the field.

Figure 1:
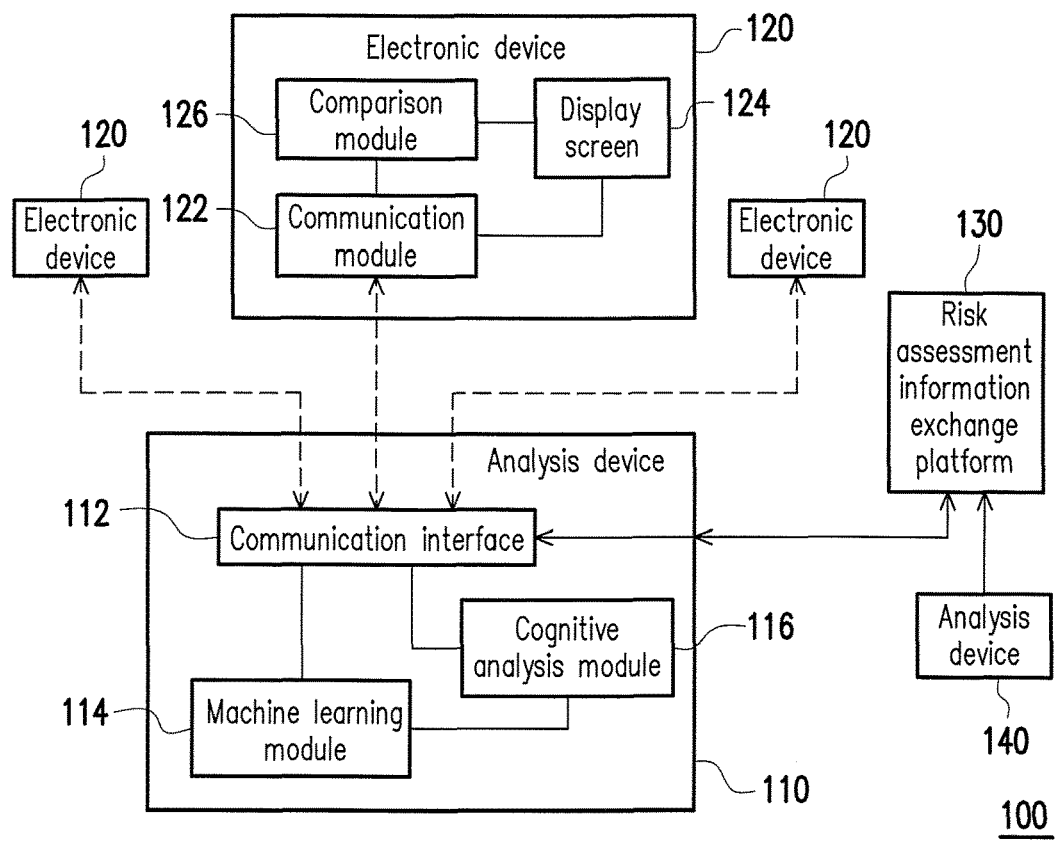
FIG. 1 is a schematic diagram of a risk assessment system according to an embodiment of the invention.

FIG. 1 is a schematic diagram of a risk assessment system 100 according to an embodiment of the invention. The risk assessment system 100 can be implemented by a corresponding structure of a cognitive analysis operation, and software defined risk assessment can be taken as a main implementation means. The risk assessment system 100 mainly includes an analysis device 110 and an electronic device 120. The analysis device 110 can be a host server or a related computer device in a specific building (for example, a hospital). In the present embodiment, the analysis device 110 mainly includes a communication interface 112, a machine learning module 114 and a cognitive analysis module 116. The communication interface 112 can be a physical network protocol or communication protocol interface card, and the analysis device 110 may communicate with and implement data transmission with other devices through the communication interface 112.

The machine learning module 114 and the cognitive analysis module 116 can be chip structures respectively implemented by respective hardware, or can be software modules implemented by one or more processors in the analysis device 110 by executing corresponding programs. The machine learning module 114 may exchange new data and a decision table generated by other analysis devices 140 with a risk assessment information exchange platform 130 and the other analysis devices 140 through the communication interface 112, and implement co-learning through a machine learning model by sharing information, such that the cognitive analysis module 116 may automatically and dynamically generate or update a decision table generated by itself. On the other hand, the machine learning module 114 may automatically and dynamically generate or update a decision table generated by itself as time passes by, such that the analysis device 110 may implement self-learning according to information (for example, medical record data of a group of people) obtained in the building (for example, the hospital). In other words, regarding a source of the data, the data can be obtained from medical records, or network databases of other hospitals on a network, a local database, an information exchange platform, questionnaires, or through medical record input or obtained through the risk assessment exchange platform 130, which is not limited by the invention. Moreover, the analysis device 110 may take the decision table obtained through self calculation as the aforementioned data for self feedback, so as to continually update the data.

The cognitive analysis module 116 may generate at least one decision table according to a plurality of data and context features of the plurality of data. Each of the decision tables has a plurality of entries, and each of the entries includes at least one determining condition and probability information corresponding to a specific result. The cognitive analysis module 116 may analyze and cluster the plurality of data according to a plurality of algorithms such as a k-means clustering algorithm, an agglomerative clustering algorithm, a reductionist clustering algorithm, etc.

The electronic device 120 is, for example, a consumer device such as a mobile phone, a tablet PC, a notebook, etc. The electronic device 120 includes a communication module 122, a display screen 124 and a comparison module 126. Each analysing device 110 can be connected to a plurality of electronic devices 120, such that a plurality of professionals of the field such as doctors may implement the embodiment of the invention through the electronic devices 120. The comparison module 126 can be a processor or a central processing unit (CPU) in the electronic device 120, and program codes can be loaded thereto to implement various steps of the embodiment of the invention. The comparison module 126 in the electronic device 120 may communicate with the analysis device 110 through the communication module 122. The communication module 122 is, for example, a data interface card or a communication chip supporting a specific data communication protocol (for example, a wireless communication, a bluetooth communication, a $3^{rd}$ generation wireless communication, a long term evolution (LTE) communication, etc.). The display screen 124 is used for displaying the decision table and the determining conditions and the probability information of each of the entries in the decision table. The electronic device 120 can be implemented by a hardware platform executing a remote application, a Java application, a graphical user interface program, a C-language application, etc.

Figure 2:
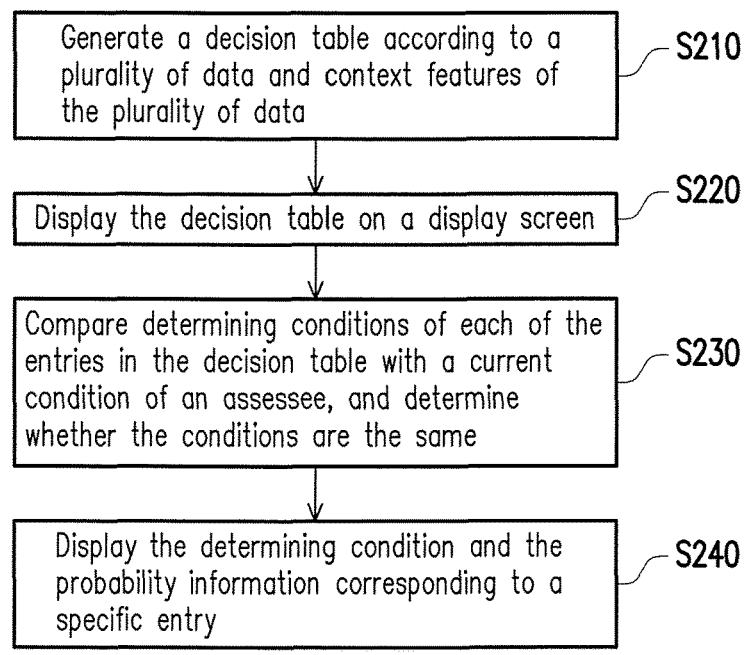
FIG. 2 is a flowchart illustrating a data processing method according to an embodiment of the invention.

FIG. 2 is a flowchart illustrating a data processing method according to an embodiment of the invention. The data processing method of the present embodiment and the risk assessment system 100 are all adapted to different fields, for example, a medical field or a crime prevention field. In order to facilitate description, the medical field is taken as an example for description. However, those skilled in the art can suitably adjust an application field according to the spirit of the embodiment of the invention. Referring to FIG. 1 and FIG. 2, it is assumed that the data processing method and the risk assessment system 100 are applied to the medical domain. In step S210, the analysis device 100 obtains a plurality of data, and generates a decision table corresponding to a specific disease or a specific situation according to the plurality of data and context features of the plurality of data. The decision table mentioned in the present embodiment can be a Bayesian rule table, and the context features of the plurality of data include one of information such as a creation time, a place, a work, a life history, a resume or a combination of the above information corresponding to a sample in each batch of the plurality of data.

The cognitive analysis module 116 may create the decision table by taking the aforementioned information in each batch of the plurality of data as a reference or determining conditions. In other words, the cognitive analysis module 116 may generate the context features of the plurality of data according to various information (for example, the creation time, place, etc.) of a plurality of samples in each batch of data, and calculate to form sample training models according to the context features. The cognitive analysis module 116 creates the decision table according to the sample training models, and calculates probability information corresponding to a specific result (for example, disease occurrence) of the decision table under different determining conditions. When a single sample is complied with a plurality of the determining conditions, such sample may simultaneously serve as a denominator or reference information of the determining conditions. For example, when two determining conditions are respectively "the age is greater than 60" and "the age is greater than 70", and the age of a sample is 75 and is complied with the aforementioned two determining conditions, the cognitive analysis module 116 simultaneously takes the sample as the denominators of the above two determining conditions. In this way, since the information of the single sample can be classified to the proper determining conditions, various data of the decision table can be more accurate.

A following decision table is taken as an example for description:

TABLE ONE

|  |  | Entry 1 | Entry 2 | Entry 3 | ... |
|---|---|---|---|---|---|
| Determination conditions | Hemiplegia | O |  |  | ... |
|  | Age is greater than 60 | O |  | O | ... |
|  | Cerebrovascular disease |  | O |  | ... |
|  | Cerebral anoxia |  |  |  | ... |
|  | Age is greater than 70 |  |  |  | ... |
| Probability of having specific disease | Have | 58.9% | 47.6% | 23.1% | ... |
|  | Not have |  |  |  |  |
| Suggestion/solution | Solution 1 | 1 |  | 1 | ... |
|  | Solution 2 | 2 | 1 | 1,2 | ... |
|  | Solution 3 |  |  | 2 | ... |

The table one of the present embodiment has a plurality of entries (for example, the entry 1 to the entry 3), and each entry is presented by a straight column in the table. Each of the entries includes at least one of the determining conditions and probability information corresponding to a specific result. For example, the table one has a plurality of determining conditions, for example, whether the sample has hemiplegia, whether the age of the sample is greater than 60, whether the sample has a cerebrovascular disease, or has cerebral anoxia or whether the sample is greater than 70, etc. The specific result in the table one is "the probability of having the specific disease".

It should be noted that each of the entries in the table one further has solutions/suggestions (i.e. the solution 1 to the solution 3 in the table) based on the entry. For example, the analysis device 110 may obtain corresponding solutions (for example, suggestions or solutions) of the specific disease from the data provided by a plurality of sources, such that the doctor is able to provide suggestions to the assessee according to the solutions. These solutions are, for example, measures suggested by the doctor that can be taken by the assessee in the future (for example, to eat less greasy, and eat more vegetables) or prescriptions provided to the assessee by the doctor. The analysing device 110 can perform a Pareto optimum operation on these solutions, such that the doctor and the assessee may have an accurate reference to take such action. In a suggestion column of the table one, different solutions have referential numbers "1", "2", and these referential numbers may represent significances of the solutions provided to the assessee by the doctor. For example, when the assessee is complied with the entry 1, the doctor or the electronic device 120 may suggest the solution 1 having the referential number "1" to the assessee in first priority, and then suggests the solution 2 having the referential number "2" to the assessee. When the assessee is complied with the entry 3, the doctor or the electronic device 120 may suggest the solution 1 and the solution 2 both having the referential number "1" to the assessee in first priority, and suggests that the solution 1 and the solution 2 are preferably carried on at the same time to achieve a better effect. Then, the doctor or the electronic device 120 suggests the solution 2 and the solution 3 both having the referential number "2" to the assessee. Moreover, the machine learning module 114 and the cognitive analysis module 116 may share data and the decision tables with other analysis devices through a network, so as to update the decision tables through a self-learning or co-learning manner.

In step S220, when the assessee (for example, a patient) inquires some hypothetical questions to a professional of a specific field (for example, the doctor), for example, "probability of having a specific disease", the doctor can use the electronic device 120 to communicate with the analysis device 110, and displays the aforementioned decision table (for example, the table one) on the display screen 124, and then the doctor or the comparison module 126 in the electronic device 120 can compare at least one current condition of the assessee with the determining conditions of each entry in the decision table. For example, a mark "O" corresponding to a determining condition on each entry of the table one facilitates the doctor to determine whether the patient is complied with such determining condition. In the present embodiment, the comparison module 126 in the electronic device 120 may automatically compare the at least one current condition of the assessee with the determining conditions of each entry in the decision table. Moreover, when the current conditions of the assessee are complied with the determining conditions of some entries, the comparison module 126 in the electronic device 120 displays the tables and at least one specific entry therein on the display screen 124. In this way, the doctor is only required to input corresponding information of the assessee, and the comparison module 126 in the electronic device 120 may automatically compare the at least one current condition of the assessee with the determining conditions of each entry in the decision table, and display the comparison result. The "current condition" of the present embodiment can be medical record data of the assessee (for example, a patient), determining data obtained by professionals of the specific field (for example, data or information obtained after observation and diagnosis of the doctor). The "current condition" can also be condition information related to the assessee that is obtained according to personal data, questionnaire, etc., filled by the assessee. Those skilled in the art can set the information source of the "current condition" according to an actual requirement.

In step S230, the doctor or the comparison module 126 compares the at least one current condition (for example, the current medical record data) of the assessee with the determining conditions of each entry in the decision table. When the current condition of the assessee (the patient) is the same with one or a plurality of determining conditions of a specific entry, a step S240 is executed, by which the comparison module 126 in the electronic device 120 displays the determining conditions and the corresponding probability information of the specific entry through the display screen 124. In this way, the doctor can explain an occurrence probability of the disease to the patient according to the determining conditions and the probability information. For example, when a certain patient is simultaneously complied with the determining conditions of "hemiplegia" and "the age is greater than 60", it represents that the patient is simultaneously complied with the entry 1 and the entry 3. Moreover, the doctor may determine the probability of having the specific disease for the entry 1 and the entry 3, so as to explain the entry with the high occurrence probability to the patient. For example, in the entry 1, the probability of having the specific disease is 58.9%, and in the entry 3, the probability of having the specific disease is 23.1%. Therefore, the doctor explains the entry 1 with the higher occurrence probability to the patient. On the other hand, when a certain patient is complied with the determining condition of "the age is greater than 60" and is not complied with the other determining conditions, it represents that the patient is complied with the entry 3, and the probability of having the specific disease is 23.1%. Therefore, the doctor explains the entry 3 to the patient. Moreover, when a patient is simultaneously complied with the determining conditions of "the age is greater than 60" and "cerebrovascular disease", it represents that the patient is simultaneously complied with the entry 2 and the entry 3. Now, the doctor explains the entry 2 with the high occurrence probability (the probability of having the specific disease is 47.6%) to the patient.

In this way, the doctor may explain to the patient that the probability of having the specific disease is probably increased due to some determining conditions according to the aforementioned table one and the determining conditions. Moreover, the doctor can provide suggestions or medicines, courses of treatment, etc., to the patient according to the suggestions/solutions listed to the bottom of each entry, so as to facilitate the doctor explaining the disease to the patient. It should be noted that in the aforementioned embodiment, although the steps S220-S240 are implemented by the professional of the specific field, in other embodiments, the steps S220-S240 can also be implemented by an application of the electronic device 120 or a user device particularly set for the use of the assesses (for example, an inquiry machine). It should be noted that the steps S220-S240 are mainly used for assisting the professional of the specific field through the electronic device 120, the comparison module 126 and the computation capability thereof.

Figure 3:
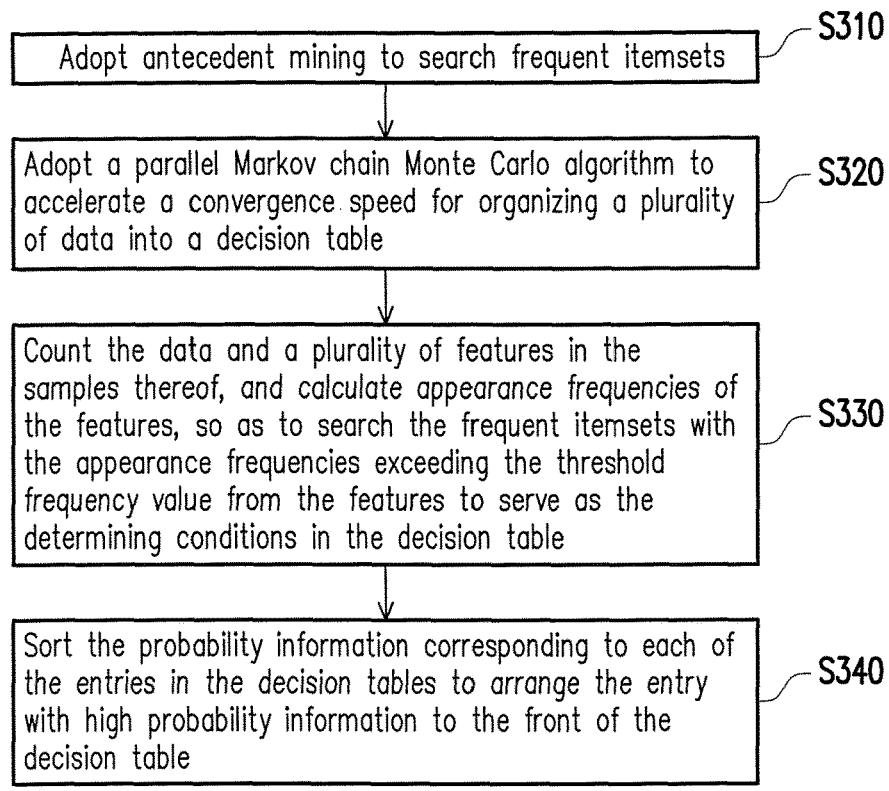
FIG. 3 is a flowchart illustrating steps of searching various determining conditions in a data processing method according to an embodiment of the invention.

In the present embodiment, the analysis device 110 may package all of the data to form a plurality of data, or the decision table complied with a Bayesian rule table specification. The analysis device 110 of the present embodiment may count the data and a plurality of features of a plurality of samples in the data through pre-calculation, and searches frequent itemsets with appearance frequencies exceeding a threshold frequency value from the features to serve as the determining conditions. Moreover, the analysis device 110 creates each of the entries in the decision table according to the determining conditions, and calculates the corresponding probability information. FIG. 3 is a flowchart illustrating steps of searching various determining conditions in a data processing method according to an embodiment of the invention. Referring to FIG. 3, in step S310, the analysis device 110 adopts antecedent mining to search the frequent itemsets, so as to decrease the number data of a feature space in the sample. In step S320, the cognitive analysis module 116 of the analysis device 110 may adopt a parallel Markov chain Monte Carlo algorithm to accelerate a convergence speed for organizing a plurality of data and samples therein into a decision table. In detail, the cognitive analysis module 116 performs Monte Carlo estimation by using a scheme of zoning and weight estimation in collaboration with independent simulation results presented by different processors, so as to implement the acceleration through a plurality of processors and monotone restriction. In step S330, the cognitive analysis module 116 counts the data and a plurality of features in the samples thereof, and calculates appearance frequencies of the features, so as to search the frequent itemsets with the appearance frequencies exceeding the threshold frequency value from the features to serve as the determining conditions in the decision table. In the present embodiment, the number of the determining conditions is not limited to one or two determining conditions presented by the aforementioned table one, but is determined by the number of the frequent itemsets with the appearance frequencies exceeding the threshold frequency value. In step S340, the analysis device 110 sorts the probability information corresponding to each of the entries in the decision tables to arrange the entry with high probability information to the front of the decision table. The electronic device 120 may sort the entries according to value magnitudes of the probability information. The comparison module 126 in the electronic device 120 may display the sorted entries on the decision table through the display screen 124, where the entry with the probability information of a high value is displayed by the electronic device 120 in first priority. Namely, the number of the determining conditions in the decision table can be derived by the analysis device 110 according to the information of each of the samples in the data and an appearance frequency thereof. In this way, the analysis device 110 may generate the aforementioned decision table, and the professional of the specific field may implement the embodiment of the invention through the electronic device 120.

On the other hand, if the embodiment of the invention is implemented by software, a single layer judgement formula can be used to increase a proportion of each batch of data for the plurality of entries, so as to avoid a situation that a single batch of data is only used in a single entry for risk estimation. In the present embodiment, each of the decision tables corresponds to a specific result, for example, each of the decision tables corresponds to a different disease occurrence rate, though a plurality of specific results can be integrated in a single decision table, so as to enhance the content of the decision table.

Figure 4:
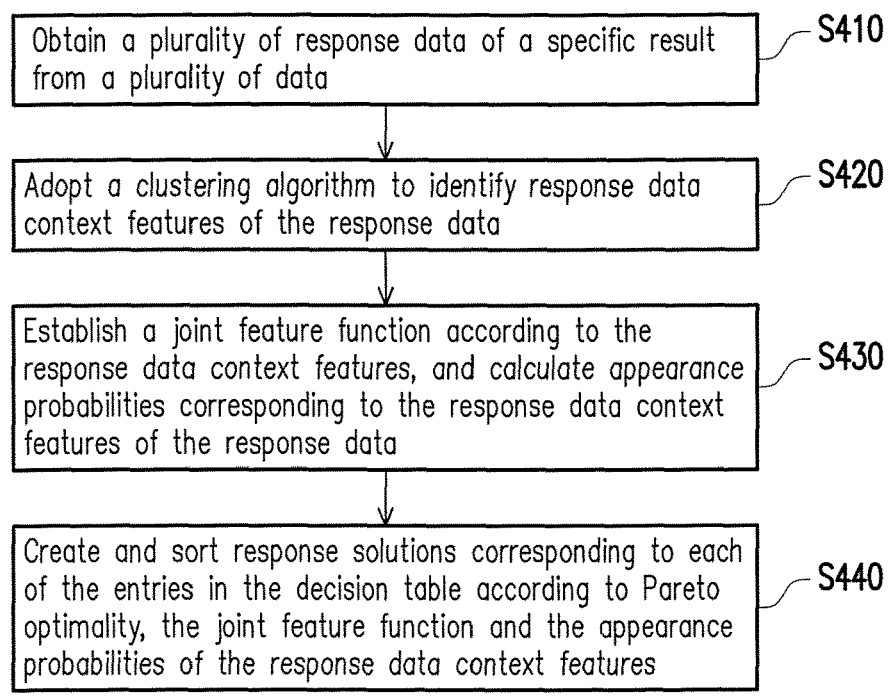
FIG. 4 is a flowchart illustrating steps of searching various response solutions/suggestions/solutions in the data processing method according to an embodiment of the invention.

FIG. 4 is a flowchart illustrating steps of searching various response solutions/suggestions/solutions in the data processing method according to an embodiment of the invention. Referring to FIG. 1 and FIG. 4, in step S410, the cognitive analysis module 116 of the analysis device 110 obtains a plurality of response data of a specific result (for example, a specific disease) from a plurality of data provided by multiple sources. In step S420, the cognitive analysis module 116 adopts a clustering algorithm to identify response data context features of the response data. In step S430, the cognitive analysis module 116 establishes a joint feature function according to the response data context features, and calculates appearance probabilities corresponding to the response data context features of the response data. In step S440, the cognitive analysis module 116 creates and sorts response solutions corresponding to each of the entries in the decision table according to Pareto optimality, the aforementioned joint feature function and the appearance probabilities of the response data context features. For example, when the appearance probability of the response data context feature of certain response data exceeds a predetermined probability value, the cognitive analysis module 116 of the embodiment of the invention may regard the response data as a response solution of one of the entries.

The cognitive analysis module 116 may adopt various methods to calculate the appearance probabilities of the response data context features in the response data, or sort the response solutions corresponding to each of the entries in the decision table. For example, the cognitive analysis module 116 may set a corresponding weight value for each of the response data context features, and adjust the appearance probabilities corresponding to the response data context features according to the weight values, so as to determine a priority sequence of the response solutions. In detail, the cognitive analysis module 116 of the analysis device 110 may calculate the weight values corresponding to the response data according to appearance frequencies of the frequent itemsets of the response data context features in the response data, and adjust the appearance probabilities corresponding to the response data context features according to the weight values corresponding to the response data, so as to adjust a sort order of a plurality of response solutions recommended in a certain entry.

Moreover, some new response data is probably neglected or ignored by the cognitive analysis module 116 due to excessively low appearance frequencies of the frequent itemsets thereof, so that in the embodiment of the invention, a weight value of the new response data can be adjusted to improve a probability that the new response data becomes the response solution. In detail, the cognitive analysis module 116 of the analysis device 110 calculates weight values corresponding to the response data according to an appearance time point of the response data. When the appearance time point of the response data is before a predetermined time point, it represents that the response data is probably old response data/response solution, so that the cognitive analysis module 116 decreases the weight values corresponding to the response data, so as to facilitate emerging of the new response data/response solution. On the other hand, when the appearance time point of the response data is behind a predetermined time point, it represents that the response data is probably new response data/response solution, so that the cognitive analysis module 116 increases the weight values corresponding to the response data. In this way, the cognitive analysis module 116 may adjust the appearance probability corresponding to the response data context feature according to the weight values corresponding to the response data.

In summary, in the risk assessment system and the data processing method of the invention, a risk assessing effect is achieved based on context features of data and a model algorithm with low complexity, so as to improve usage efficiency. On the other hand, a professional in the field such as a doctor, etc., may explain a risk assessment reason and a prevention method of a specific event to the assessee or patient through the determining conditions, such that the risk assessment system is easy to use.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:

1. A risk assessment system, comprising:
   an analysis device, generating at least one decision table according to a plurality of data and context features of the plurality of data, wherein each of the decision tables has a plurality of entries, and each of the entries comprises at least one determining condition and probability information corresponding to a specific result; and
   an electronic device, communicating with the analysis device, receiving the at least one decision table, and comparing the at least one determining condition of each of the entries in the at least one decision table with at least one current condition of an assessee, wherein when the at least one current condition is the same with the at least one determining condition of at least one specific entry, the electronic device displays the at least one determining condition and the probability information corresponding to the at least one specific entry, to improve a usage efficiency of the at least one decision table.

2. The risk assessment system as claimed in claim 1, wherein the analysis device obtains the plurality of data according to information obtained through a network database, a local database, an information exchange platform, or a questionnaire, and the analysis device self feeds back the at least one decision table to obtain the plurality of data.

3. The risk assessment system as claimed in claim 1, wherein the analysis device shares the plurality of data and the at least one decision table with other analysis device through a network.

4. The risk assessment system as claimed in claim 1, wherein the at least one decision table is a Bayesian rule table, and the context features of the plurality of data comprise one of information such as a creation time, a place, a work, a life history, a resume or a combination of the above information corresponding to a sample in each batch of the plurality of data.

5. The risk assessment system as claimed in claim 1, wherein the analysis device automatically obtains a plurality of new data or other decision table to dynamically generate or update the at least one decision table.

6. The risk assessment system as claimed in claim 1, wherein the analysis device counts the plurality of data and the context features in the plurality of data, searches frequent itemsets with appearance frequencies exceeding a threshold frequency value from the context features to serve as the at least one determining condition, creates each of the entries in the at least one decision table according to the at least one determining condition, and calculates the corresponding probability information.

7. The risk assessment system as claimed in claim 1, wherein the analysis device comprises:
   a communication interface;
   a machine learning module, coupled to the communication interface to obtain the plurality of data from at least one source, wherein the machine learning module performs self-learning, and implements co-learning by sharing the plurality of data; and
   a cognitive analysis module, coupled to the machine learning module and the communication interface, and receiving the plurality of data and analyzing the context features in the plurality of data, so as to generate or update the at least one decision table according to the plurality of data and the context features.

8. The risk assessment system as claimed in claim 1, wherein the electronic device comprises:
   a communication module, wherein the electronic device communicates with the analysis device through the communication module; and a display screen, displaying the at least one decision table, a part of the entries in the at least one decision table and the probability information corresponding to the specific result.

9. The risk assessment system as claimed in claim 8, wherein the electronic device further comprises:
a comparison module, coupled to the communication module and the display screen, and comparing the at least one determining condition of each of the entries in the at least one decision table with the at least one current condition of the assessee, wherein when the at least one current condition is the same with the at least one determining condition of the at least one specific entry, the display screen displays the at least one determining condition and the probability information corresponding to the at least one specific entry.

10. The risk assessment system as claimed in claim 1, wherein the electronic device displays the at least one sorted specific entry, wherein the at least one specific entry with the probability information of a high value is displayed by the electronic device in first priority.

11. The risk assessment system as claimed in claim 1, wherein each of the entries further comprises at least one response solution corresponding to the specific result.

12. The risk assessment system as claimed in claim 11, wherein the analysis device obtains a plurality of response data of the specific result from the plurality of data, adopts a clustering algorithm to identify response data context features in the response data, establishes a joint feature function according to the response data context features, and calculates appearance probabilities corresponding to the response data context features, and creates and sorts the response solutions corresponding to each of the entries in the decision table according to Pareto optimality, the joint feature function and the appearance probabilities of the response data context features.

13. The risk assessment system as claimed in claim 12, wherein the analysis device calculates weight values corresponding to the response data according to frequent itemsets of the response data context features of the response data, and adjusts the appearance probabilities corresponding to the response data context features according to the weight values corresponding to the response data.

14. The risk assessment system as claimed in claim 12, wherein the analysis device calculates weight values corresponding to the response data according to an appearance time point of the response data, and adjusts the appearance probabilities corresponding to the response data context features according to the weight values corresponding to the response data.

15. A data processing method, comprising:
generating at least one decision table according to a plurality of data and context features of the plurality of data, wherein each of the decision tables has a plurality of entries, and each of the entries comprises at least one determining condition and probability information corresponding to a specific result;
comparing the at least one determining condition of each of the entries in the at least one decision table with at least one current condition of an assessee; and
displaying the at least one determining condition and the probability information corresponding to at least one specific entry when the at least one current condition is the same with the at least one determining condition of the at least one specific entry, to improve a usage efficiency of the at least one decision table.

16. The data processing method as claimed in claim 15, further comprising:
obtaining the plurality of data according to information obtained through a network database, a local database, an information exchange platform, or a questionnaire, or by self feeding back the at least one decision table.

17. The data processing method as claimed in claim 15, further comprising:
sharing the plurality of data and the at least one decision table with other analysis device through a network.

18. The data processing method as claimed in claim 15, wherein the at least one decision table is a Bayesian rule table, and the context features of the plurality of data comprise one of information such as a creation time, a place, a work, a life history, a resume or a combination of the above information corresponding to a sample in each batch of the plurality of data.

19. The data processing method as claimed in claim 15, further comprising:
automatically obtaining a plurality of new data or other decision table to dynamically generate or update the at least one decision table.

20. The data processing method as claimed in claim 15, wherein the step of generating the at least one decision table comprises:
counting the plurality of data and the context features in the plurality of data;
searching frequent itemsets with appearance frequencies exceeding a threshold frequency value from the context features to serve as the at least one determining condition; and
creating each of the entries in the at least one decision table according to the at least one determining condition, and calculating the corresponding probability information.

21. The data processing method as claimed in claim 15, wherein the step of displaying the at least one determining condition and the probability information corresponding to the at least one specific entry comprises:
displaying the at least one specific entry with the probability information of a high value in first priority.

22. The data processing method as claimed in claim 15, wherein each of the entries further comprises at least one response solution corresponding to the specific result.

23. The data processing method as claimed in claim 22, wherein the step of generating the at least one decision table according to the plurality of data and the context features of the plurality of data comprises:
obtaining a plurality of response data of the specific result from the plurality of data;
adopting a clustering algorithm to identify response data context features in the response data;
establishing a joint feature function according to the response data context features, and calculating appearance probabilities corresponding to the response data context features of the response data; and
creating and sorting the response solutions corresponding to each of the entries in the decision table according to Pareto optimality, the joint feature function and the appearance probabilities of the response data context features.

24. The data processing method as claimed in claim 23, wherein the step of calculating the appearance probabilities corresponding to the response data context features of the response data comprises:

calculating weight values corresponding to the response data according to frequent itemsets of the response data context features of the response data; and adjusting the appearance probabilities corresponding to the response data context features according to the weight values corresponding to the response data.

25. The data processing method as claimed in claim 23, wherein the step of calculating the appearance probabilities corresponding to the response data context features of the response data comprises:

calculating weight values corresponding to the response data according to an appearance time point of the response data; and adjusting the appearance probabilities corresponding to the response data context features according to the weight values corresponding to the response data.

* * * * *